(12) United States Patent
Birkbeck et al.

(10) Patent No.: US 7,727,237 B2
(45) Date of Patent: Jun. 1, 2010

(54) BONE CLAMP

(75) Inventors: Alec Birkbeck, Leeds (GB); Callum Colquhoun, Halifax (GB); Peter Goodwin, Lincoln (GB)

(73) Assignee: Depuy International Ltd. (GB)

( * ) Notice: Subject to any disclaimer, the term of this patent is extended or adjusted under 35 U.S.C. 154(b) by 1207 days.

(21) Appl. No.: 11/018,623

(22) Filed: Dec. 21, 2004

(65) Prior Publication Data

US 2005/0149028 A1 Jul. 7, 2005

(51) Int. Cl.
*A61F 5/00* (2006.01)
(52) U.S. Cl. .............................. 606/87; 606/96; 606/104
(58) Field of Classification Search ................... 606/57, 606/86, 86 R, 87, 88, 105; 269/86, 89, 104, 269/107, 216, 217, 238
See application file for complete search history.

(56) References Cited

U.S. PATENT DOCUMENTS 5,732,992 A * 3/1998 Mauldin .................. 294/119.1

FOREIGN PATENT DOCUMENTS

JP 2000287983 A 10/2000

OTHER PUBLICATIONS

Takahiro, Seki; Japanese Patent 200287983A; Mizuho Co. Ltd, Oct. 17, 2000; English Abstract; MicroPatent Report; www.micropat.com; 2009.

* cited by examiner

*Primary Examiner*—Thomas C Barrett
*Assistant Examiner*—Andrew Yang

(57) ABSTRACT

A bone clamp for securing a surgical instrument to a bone including a body on which the instrument can be mounted, a first and second contacting arms, each of which has a first end that is pivotally connected to the body, and a second end for gripping the bone, whenever the first and second contacting arms are connected to the body at or towards opposite ends thereof so that, when the body is positioned adjacent to the bone, the arms can grip the bone on opposite surfaces thereof, and an actuator which can be moved between engaged and disengaged positions. When the actuator is in its disengaged position, the contacting arms can pivot independently with respect to each other, and when the actuator is in its engaged position, the pivoting movement of one contact arm is accompanied by approximately equal pivoting movement of the other contact arm in the opposite direction.

20 Claims, 2 Drawing Sheets

BONE CLAMP

BACKGROUND

This invention relates to a bone clamp for securing a surgical instrument to a bone.

A bone can be prepared to receive a component of an orthopaedic joint prosthesis using a surgical instrument. For example a surgical instrument can be used to resect a bone so that it is appropriately shaped to fit the prosthesis component. It can be important that the location and dimensions of the resection are controlled accurately to ensure a precise fit of the prosthesis component on the resected bone. In order to optimise the accuracy of a resection or other preparatory step, it is known to use a guide block which can be fixed relative to the bone. The guide block should be positioned accurately relative to the bone. It should also be fixed against movement during the resection or other procedure.

A guide block for a surgical instrument can be fixed to a bone using pins or screws or similar fasteners, which penetrate the bone. This can require a drilling step to prepare the bone to receive the fasteners.

SUMMARY

The present invention provides a bone clamp which can be fastened against movement relative to a bone using arms which can grip the bone on opposite sides thereof.

Accordingly, in one aspect, the invention provides a bone clamp for securing a surgical instrument to a bone comprising: a body on which the instrument can be mounted; first and second contacting arms, each of which has a first end at or towards which the arm is pivotally connected to the body, and a second end for gripping the bone, in which the first and second contacting arms are connected to the body at or towards opposite ends thereof so that, when the body is positioned adjacent to the bone, the arms can grip the bone on opposite surfaces thereof; and an actuator which can be moved between engaged and disengaged positions; in which when the actuator is in its disengaged position, the contacting arms can pivot independently with respect to each other, and when the actuator is in its engaged position, the pivoting movement of one contact arm is accompanied by approximately equal pivoting movement of the other contact arm in the opposite direction.

The arms can be moved pivotally relative to the clamp body, independently of one another to while the clamp is being positioned relative to the bone, and simultaneously through equal angles but in opposite directions to tighten the clamp on to the bone.

The bone clamp of the present invention has the advantage that it enables the steps of (a) locating the clamp on the bone, and (b) fixing the clamp to the bone, to be separated. The initial step of locating the clamp on the bone can be carried out while the actuator is in the disengaged position, allowing the contacting arms to be moved independently of one another until they contact the bone. This can take into account, for example, anatomical variations between patients, variation in the position or orientation or both of the clamp, use of the clamp on, for example a left limb or a right limb. Once the clamp has been positioned as desired, it can be secured to the bone in that position by moving the actuator to the engaged position in which movement of one of the arm on one end of the clamp body is accompanied by approximately equal pivoting movement of the other arm in the opposite direction. By virtue of the equal movement in the opposite direction, the position of the clamp is not affected significantly by the securing step. This increases the ease of securing the bone clamp to the bone because it eliminates the need for the surgeon to tighten one arm, and then the other, alternately in order to ensure a secure grip on the bone is achieved. Furthermore, the body does not twist, or shift from its original location, and therefore enhances the accuracy with which the bone clamp is secured to the bone.

The bone clamp of the present invention also has the advantage that it is versatile. The ability to move the contacting arms independently, while the actuator is in its disengaged position, enable the bone clamp to be adapted for securing to different bone shapes, while ensuring that the surgeon has full control over the orientation and location of the body of the bone clamp. For example, by adjusting the arms independently, a bone clamp according to the present invention can be configured to clamp to a right femur, and subsequently be configured to clamp to a left femur, without the orientation and location of the body of the clamp being compromised.

The bone clamp can be used to fasten a surgical instrument such as a guide block to a bone. The bone clamp can itself be used as a surgical instrument such as a guide block. A guide block can have features on it which can be engaged by another surgical instrument during a surgical procedure, especially a cutting instrument, for example an instrument to cut a bore such as a drill or a reamer or a resecting instrument such as a saw.

When the bone clamp is used to fasten a surgical instrument to a bone, it is preferably arranged so that the instrument can be fastened securely to the bone clamp. For example, one of the instrument and the clamp can have at least one recess formed in it, and the other can include one or more matching projections, each of which can be received in a corresponding recess. When there is just one recess and corresponding projection, they will often have a non-circular cross-section so that relative rotation is inhibited. Preferably, the bone clamp and the instrument can be locked against inadvertent separation, for example using a latch or other mechanism.

The bone clamp can be configured so that a plurality of surgical instruments can be mounted on it.

Preferably, the shape of the first contacting arm is approximately the same as the shape of the second contacting arm, but for it being a mirror image thereof, so that movement the second end of the first arm while the actuator is in the engaged position results in corresponding movement of the second end of the second arm, through the same distance and angle of articulation. The first and second contacting arms can be substantially straight. However, the first and second contacting arms need not be substantially straight. For example, each of the first and second contacting arms can comprise more than one straight part, angled relative to each other, so that the first and second contacting arms each define a rectilinear path having more than one straight line. Preferably, the rectilinear path is such that the first and second ends of each of the arms are not coplanar with respect to the plane perpendicular to axis of the bone, when the bone clamp is accordingly positioned adjacent the bone.

Alternatively, the first and second contacting arms may be curved. Preferably, the first and second contacting arms are curved such that the first and second ends of each of the arms are not coplanar with respect to the plane perpendicular to axis of the bone, when the bone clamp is accordingly positioned adjacent the bone. Preferably, at least a portion of the first and second contacting arms is approximately straight and a portion is curved; for example, the first and second contacting arms can be approximately straight towards their first end and curved towards their second end.

The faces of the arms of the contacting arms which face towards one another can be concave, which has been found to facilitate fitting of the clamp on to a bone.

Preferably, the bone clamp comprises a second pair of first and second contacting arms, in addition to the first pair of first and second contacting arms described above. More preferably, the bone clamp comprises more than two pairs of first and second contacting arms. Preferably, the first contacting arms of the bone clamp pivot about a common axis, and the second contacting arms of the bone clamp pivot about a common axis.

When the bone clamp comprises a second pair of first and second contacting arms, preferably, the second pair of first and second contacting arms are not identical.

When the bone clamp comprises a second pair of first and second contacting arms, preferably, the second ends of the first contacting arms are displaced away from each other in a plane parallel to the length of the axis about which the first arms pivot. Preferably, the second ends of the second contacting arms are displaced away from each other in a plane parallel to the length of the axis about which the second arms pivot.

It has been found that where there is more than one pair of first and second contacting arms, the combination of a substantially straight pair of first and second contacting arms, and a pair of first and second contacting arms having a second end laterally displaced from the first end in a direction parallel to the longitudinal axis of the bone, when the bone clamp is accordingly positioned adjacent the bone, improves the stability of the bone clamp. Preferably, the second end of the contacting arms are displaced from the first end in a direction parallel to the longitudinal axis of the bone, and in a direction away from the side of the bone clamp on which the surgical instrument can be mounted so that the contacting arms do not obstruct the part of the bone on which the surgical instrument is to operate.

Preferably, the first end of each contacting arm is pivotally connected to the body by way of a hinge mechanism. Preferably, a contacting arm is pivotally connected to the body so that it is pivotable around an axis which extends generally parallel to the length of the bone, when the bone clamp is accordingly positioned adjacent the bone. Preferably, a bore extends through the arm at or towards its first end. Preferably, a bore extends through the body where the contacting arm is to be pivotally attached to the body, so that when the contacting arm is pivotally attached to the body, the bore of the contacting arm and the bore of the body have a common axis. A pivot pin can then pass through the bore of the body and the bore of the contacting arm, so that the contacting arm is pivotable about the axis defined by the bore therein.

Preferably, the second end of each contacting arm comprises means for gripping a bone. Preferably, the gripping means comprises at least one sharp projection which can penetrate the surface of the bone. More preferably the gripping means comprises a plurality of sharp projections. When the gripping means is provided by relatively few projections, it will be expected that they will have to penetrate the surface bone to a greater degree then when the gripping means is provided by several projections, so that gripping means which is provided by a serrated or otherwise roughened area on the second end of the contacting arms can rely largely on frictional engagement with the bone.

Preferably, each of the contacting arms has a gear mechanism at or towards its first end. Preferably, each of the arms presents an array of gear teeth arranged radially around its respective pivot axis so as to form a part worm wheel of a worm gear assembly.

Preferably, the bone clamp includes a threaded shaft extending between the gear mechanisms for the first and second contacting arms. Preferably the shaft has a substantially uniform cross-section along its length. Preferably, the cross-section of the shaft along its length is generally circular.

Preferably, the shaft is configured at one of its ends so that it can be engaged in order to impart a rotational force to it to cause it to rotate about its axis. For example, the shaft can have a non-circular recess (for example hexagonal or star shaped or slotted or cross-shaped) formed in it at its end for receiving a driver having a correspondingly shaped end which can be received in the recess. Such a recess can be provided at each of the ends of the shaft.

The thread on the shaft will generally be on its external surface. Preferably the shaft has a first thread extending from one end of the shaft towards the middle, and a second thread extending from the other end of the shaft towards the middle, in which one of the shaft threads is a left hand thread and the other of the shaft threads is a right hand thread. Preferably the pitches of the first and second threads are equal. Preferably, the shaft has a non-threaded middle part. Preferably, the non-threaded middle part has a smaller cross-section than the threaded parts either side of the middle part.

The shaft can be provided by more than one elongate cylindrical member. For example, the shaft can be provided two or more elongate cylindrical members which are joined together so that they have a common axis. Especially preferably, the shaft comprises two elongate cylindrical members, joined by a third elongate cylindrical member so that they all have a common axis, wherein the third elongate cylindrical member has a diameter smaller than the diameter of the other cylindrical members. Preferably, the third elongate cylindrical member has a smooth surface. The shaft can be made from any material suitable for use during surgery. Particularly preferred materials can include certain stainless steels.

Preferably, the actuator acts on the shaft when the actuator is in its engaged position, to urge the shaft against the gears on the contacting arms. Preferably, the actuator comprises a bar which extends along the clamp body, and in which (a) when the actuator is in the engaged position, the bar clamps the shaft tightly between it and the body so that the shaft is urged against the said gears, and (b) when the actuator is in the disengaged position, the shaft is able to move away from the gears. The actuator can be made from any material suitable for use during surgery. Particularly preferred materials can include certain stainless steels.

When the bone clamp comprises a second pair of first and second contacting arms, preferably, the bone clamp includes a second threaded shaft extending between the gear mechanisms of the second pair of first and second contacting arms.

Preferably, the actuator includes a nut which engages an elongate threaded member extending from the body, which can be tightened to move the bar towards the clamp body. Preferably, the elongate member projects through the bar so that the bar is positioned between the nut and the body. Preferably, the bar is biassed towards the body. For example, the actuator can include an elastic member which acts to force the bar towards the body. Preferably, the elastic member is a spring. Biassing the bar towards the body has the advantage that the shaft can be maintained in contact with the gears on the contacting arms, providing some resistance to free movement of the contacting arms relative to the body. When the actuator is in the release position, this resistance can be overcome by forcing the bar away from the body, against the resistance provided by the biassing means.

When the bone clamp comprises a second pair of contacting arms, preferably, the elongate threaded member passes between the shafts extending between the gear mechanisms of the contacting arms. Preferably, the elongate threaded member has two parallel flat sides which are not threaded. Preferably, the flat sides are smooth. When the bone clamp comprises a second pair of contacting arms, preferably, the elongate threaded member passes between the middle parts of the shafts.

Alternatively, the bone clamp may include electronic components connected to mechanical components associated with each arm for driving the pivoting action of the arm. Preferably, when the actuator is in its engaged position, the pivoting of one contacting arm generates a signal in the electronic components which then drive the mechanical components of the other contacting arm to move the arm accordingly, and when the actuator is in its disengaged position, the pivoting of one contacting arm does cause the other contacting arm to be moved. Preferably, the actuator comprises a switch. Examples of materials which can be used to form parts of the bone clamp, such as any of the body, the contacting arms, the bar, the biassing means, and the shaft, include metals such as stainless steels, and polymers, such as are commonly used in the manufacture of surgical instruments.

BRIEF DESCRIPTION OF THE DRAWINGS

An embodiment of the invention will now be described by way of example with reference to the accompanying drawings.

DETAILED DESCRIPTION

Figure 1:
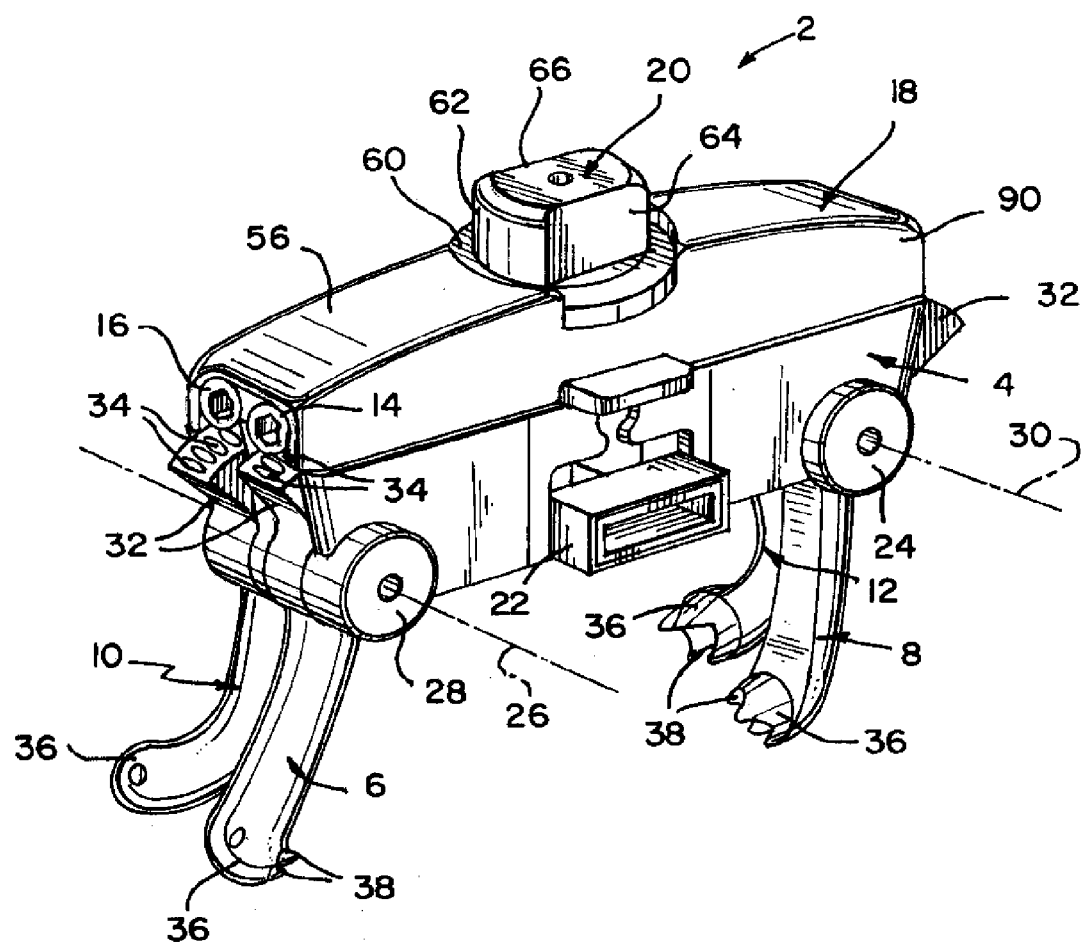
FIG. 1 shows an isometric view of the bone clamp according to the present invention.
Figure 2:
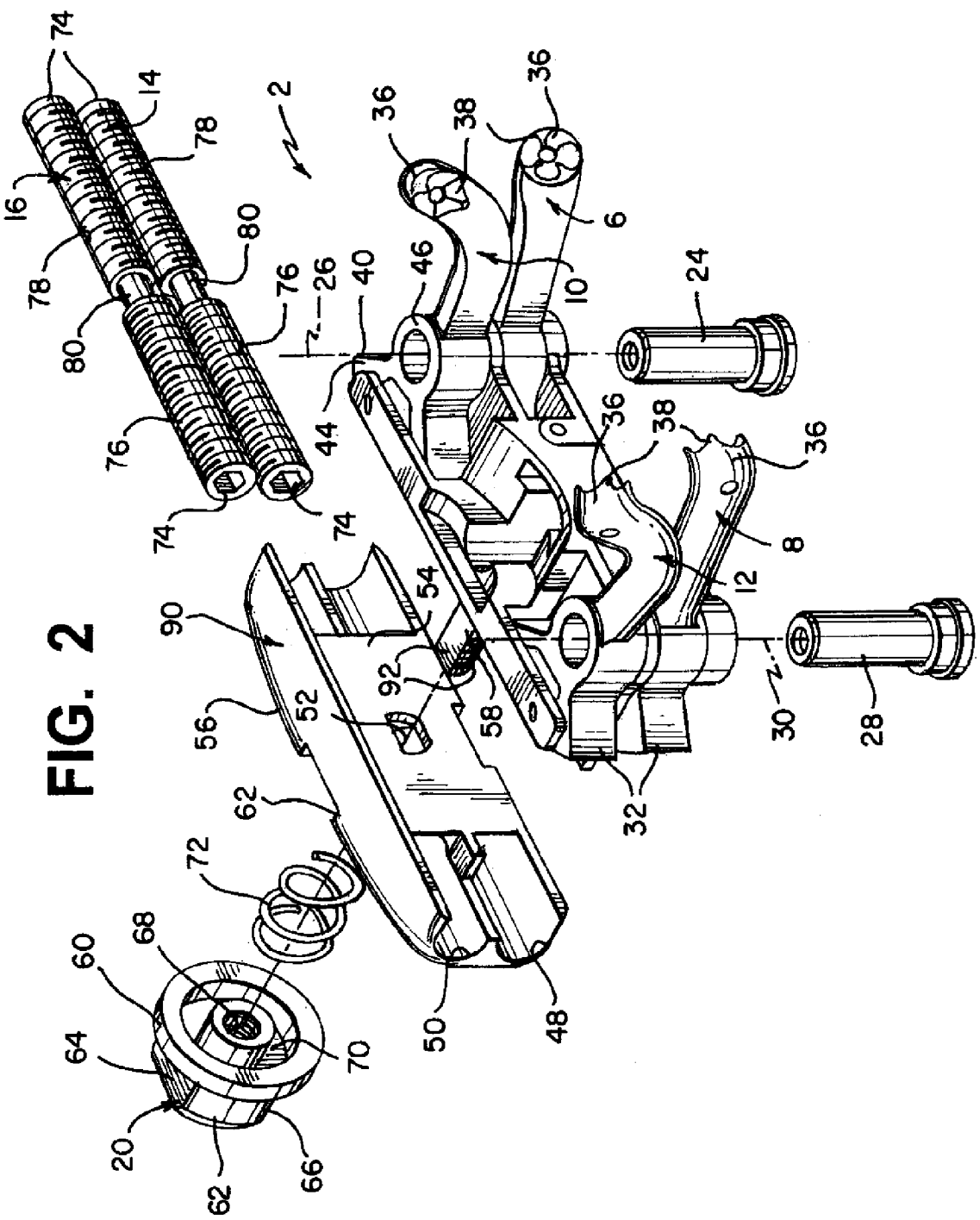
FIG. 2 shows an isometric view of the various components of the bone clamp of FIG. 1.

Referring to the drawings, FIGS. 1 and 2 show a bone clamp 2. The bone clamp 2 has a body 4 for extending across a bone (not shown) with a socket 22 for releasably securing a surgical instrument (not shown). First 6, second 8, third 10, and fourth 12 contacting arms, each contacting arm having a first end proximal to the body 4 and a second end distal to the body 4; first 14 and second 16 threaded shafts; and actuator 18 having an actuating nut 20.

The body 4 comprises one piece made of surgical stainless steel. The first and third contacting arms 6, 10 and are pivotally attached towards one end of the body 4 and the second and fourth contacting arms 8, 12 are pivotally towards the opposite end of the body 4, so that the contacting arms are located on either side of the bone when the bone clamp is accordingly located adjacent the bone. The mechanism for pivotally attaching the contacting arms 6, 8, 10, 12 to the body is described in more detail below. The body 4 also has a socket 22 on its front side for receiving and securing a surgical instrument to the body. The socket 22 is located between the sides of the body 4 towards which the contacting arms 6, 8, 10, 12 are attached. A latch (not shown) can secure an instrument to the body, in which the construction of such instruments which will be known to the skilled reader.

The first and third contacting arms 6, 10 are retained within the body 4 by a first smooth cylindrical shaft 24 which extends though a bore within each of the contacting arms and a first bore within the body, so that the contacting arms are pivotable relative to the body about a common axis 26. The bores within the first and third contacting arms 6, 10 and the body 4 have substantially identical diameters as the diameter of the cylindrical shaft 24. The bore within each of the first and third contacting arms 6, 10 is located towards the first end of the arm, and the first bore within the body is located towards a first side of the body 4. The first and third contacting arms 6, 10 are not fixed to each other and therefore they can pivot independently with respect to each other.

The second and fourth contacting arms 8, 12 are retained within the body 4 by a second smooth cylindrical shaft 28 which extends though bores within the contacting arms and a second bore within the body, so that the contacting arms are pivotable relative to the body about a common axis 30. Again, the bores within the second and fourth contacting arms 8, 12 and the second bore within the body 4 have substantially identical diameters as the diameter of the first cylindrical shaft 28. The bore within each of the second and fourth contacting arms 8, 12 is located towards the first end the arm, and the second bore within the body is located towards a second side of the body 4, opposite to the first side. The second and fourth contacting arms 8, 12 are not fixed to each other and therefore they can pivot independently with respect to each other.

As shown, first and second contacting arms 6, 8 have approximately the same shape but for them being mirror images of each other, and third and fourth contacting arms 10, 12 have approximately the same shape but for them being mirror images of each other.

The first and second contacting arms 6, 8 are substantially straight along their length. In contrast, the third and fourth contacting arms 10, 12 are curved such that the first and second ends of each of the third and fourth contacting arms 10, 12 are not coplanar with respect to the plane perpendicular to axis of the bone.

Each contacting arm 6, 8, 10, 12 comprises a part worm wheel gear mechanism 32 situated at its first end. The part worm wheel gear mechanism 32 has a plurality of teeth 34. The part worm wheel gear mechanism 32 slightly protrudes the top of the body 4 when the contacting arm 6, 8, 10, 12 is held in position within the body.

Each contacting arm 6, 8, 10, 12 further comprises a gripping arrangement 36 at its second end for gripping the bone. The gripping arrangement 36 comprises a plurality of sharp projections 38 extending perpendicularly away from the arm, for penetrating the surface of the bone. As can be seen from the figures, the first 6 and third 10 contacting arms are arranged for gripping one side of the bone, and second 8 and fourth 12 contacting arms are arranged for gripping the opposite side of the bone.

The actuator 18 is separate from body 4 (as best seen in FIG. 2) and comprises a bar 90 and an actuating nut 20. The length and width of the bar 90 is substantially identical to the body 4, so that it can extend along and across the body. The bar 90 comprises first and second passageways 48, 50 extending parallel to one another, along the entire length of the bar 90. The underside 54 of the bar 90 is cut away at either end so that the ends of the first and second passageways 48, 50 are exposed. The bar 90 further comprises an opening 52 extending from the middle of the underside 54 of the bar, to the middle of the upperside 56 of the actuator, and passes between the first and second passageways 48, 50. A threaded projection 58, in the form of an M8 post having two smooth flat parallel sides 92, extending from the body 4 can be received by the opening 52 so that the threaded projection extends through the bar 90 and protrudes the upperside 56 of the actuator. The actuating nut 20 comprises a circular base 60 and a generally circular head 62, in which the head has two flat opposing sides 64 and 66. The circular base 60 of the actuating nut 20 can be received within a circular recess 60 on the upperside 56 of the bar 90 so that the actuating nut is rotatable within the recess. The actuating nut 20 further comprises a threaded bore 68, extending from its underside towards its upperside, for receiving threaded projection 58, and a circular recess 70 on its underside for accommodating one end of a wound spring 72.

When the bar 90 is positioned on the body 4 so that the threaded projection 58 extends through the opening 52 and engages the threaded bore 68, the helically wound spring 70 is located between the actuating nut and the actuator so as to bias the actuating nut away from the actuator. Therefore, as the actuating nut 20 is tightened and travels along the threaded projection 58 towards the body 4, the helically wound spring 72 is compressed against the bar 90 and, as a result of the helically wound spring resisting the compression, the spring thrusts the actuator towards the body. When the actuating nut 20 has been fully tightened, the actuator 18 is in its engaged position. As the actuating nut 20 is loosened and travels along the threaded projection 58 away from the body 4, the compressive force on the helically wound spring 72 is removed and therefore the thrust on the bar 90 is also removed. When the actuating nut 20 has been fully loosened, the actuator 18 is in its disengaged position.

The first passageway 48 of the actuator can receive a first shaft 14 which extends between the first ends of first and second contacting arms 6, 8, and the second passageway 50 of the actuator can receive a second shaft 16 which extends between the first ends of third and fourth contacting arms 10, 12.

The first shaft 14 has recesses 74 at both of its ends. The cross section of each recess 74 is hexagonal so that each end of the bore can be engaged by a hexagonal tool. The first shaft 14 has a right handed threaded portion 76 extending from one end of the shaft towards its middle, and a left threaded portion 78 extending from the opposite end of the shaft towards its middle. The pitches and the diameters of the left and right threaded portions 76, 78 are equal. The first shaft 14 further comprises a smooth shank 80 between the two threaded portions 76, 78 which has a diameter smaller than the diameter of the threaded portions. The first and second shafts 14, 16 are identical in configuration.

It will be appreciated that the diameter of the smooth shanks 80 of the first and second shafts 14, 16 are such that when the bar 90 is positioned on the body 4 so that the threaded projection 58 extends through the passageway 52, the threaded projection 58 is capable of passing between the smooth shanks of the shafts. It will be appreciated that the width of the threaded projection 58 between the two flat sides 92, is small enough so that the threaded projection is capable of passing between the smooth shanks 80 of first and second shafts 14, 16 but large enough to function as a key to retain the shafts within the bar 90, while allowing the shafts to rotate freely within the bar.

When the actuator 18 is in its disengaged position, the threads of the first and second shafts 14, 16 engage the teeth of the worm wheel gear mechanisms 32 at the first ends of the first and second contacting arms 6, 8, and third and fourth contacting arms 10, 12 respectively. However, the helically wound spring 72 does not thrust on the bar 90, and therefore the bar is able to move away from the body 4. Therefore, if the surgeon pivots any of the contacting arms 6, 8, 10, 12, the teeth 34 of the worm wheel gear mechanism 32 on the arm being pivoted, which engage the thread of a shaft, forces the shaft away from body 4 to which the arm is fixed, and thereby forces the bar 90 away from the body. Once the shaft has been forced away from the body so that its thread no longer engages the teeth 34 of the worm wheel gear mechanism 32 (i.e. the peak of the thread and the peak of the teeth are abutting), the arm is free to pivot by an amount equivalent to the pitch of the teeth/thread. This pivoting action can be repetitively performed until the arm is in its desired location. Therefore, each arm is free to pivot independently.

When the actuator 18 is in its engaged position, the threads of the first and second shafts 14, 16 engage the teeth of the gear mechanisms 32 at the first ends of the first and second contacting arms 6, 8, and third and fourth contacting arms 10, 12 respectively. However, as the helically wound spring 72 thrusts the bar 90 against the body 4 in the engaged position, the threads of the first and second shafts 14, 16 are forced against the teeth of the gear mechanisms 32 and the first and second shafts 14, 16 act as a worm drive against the gear mechanisms 32 of first and second contacting arms 6, 8 and third and fourth contacting arms 10, 12, respectively. Therefore, the first and second contacting arms 6, 8 can be pivoted in unison by rotating the first shaft 14 with the use of a tool (not shown) having a hexagonal end which can be received by the hexagonal recesses 74 within the shaft. As the left threaded portion 78 of the first shaft 14 engages the worm wheel gear mechanism 32 of first contacting arm 6 and the right threaded portion 76 of the first shaft 14 engages the worm wheel gear mechanism 32 of second contacting arm 8, both contacting arms pivot together. Further, as the one of the threaded portions is a right handed thread, and the other is a left handed thread, the pivoting movement of one contact arm is accompanied by approximately equal pivoting movement of the other contact arm in the opposite direction.

If the surgeon attempts to pivot any of the first or second contacting arms 6, 8 or third or fourth contacting arms 10, 12 by applying a force directly on the contacting arm when the actuator 18 is in the engaged position, the first shaft 14 or second shaft 16 with which that contacting arm is engaged with will not be able to be forced away from the contacting arm due to the helically wound spring 72 acting on the bar 90 which retains the shaft. Therefore the contacting arm will not be free to pivot.

The invention claimed is:

1. A bone clamp for securing a surgical instrument to a bone, comprising:
   a body on which the instrument can be mounted;
   first and second contacting arms, each of which has a first end pivotally connected to the body, the first ends each having a plurality of teeth, and a second end for gripping the bone, wherein the first and second contacting arms are connected to the body at or towards opposite ends thereof and are configured such that, when the body is positioned adjacent to the bone, the arms can grip the bone on opposite surfaces thereof; and
   an actuator movable between an engaged position and a disengaged position, wherein when the actuator is in the disengaged position, the first and second contacting arms are configured to pivot independently with respect to each other, and when the actuator is in the engaged position, the actuator engages the plurality of teeth of the first and second contacting arms such that the pivoting movement of one contact arm is accompanied by approximately equal pivoting movement of the other contact arm in the opposite direction.

2. The bone clamp of claim 1, comprising a first gear mechanism operably connected to the first contacting arm at or towards the first end of the first contacting arm and a second gear mechanism operably connected to the second contacting arm at or towards the first end of the second contacting arm.

3. The bone clamp of claim 2, wherein the actuator comprises a threaded shaft extending between and engaging the first gear mechanism and the second gear mechanism.

4. The bone clamp of claim 3, wherein the threaded shaft has a first thread extending from one end of the shaft towards the middle, and a second thread extending from the other end of the shaft towards the middle, and wherein one of the shaft threads is a left hand thread and the other of the shaft threads is a right hand thread.

5. The bone clamp of claim 3, wherein the actuator comprises a nut and the nut acts on the shaft when the actuator is in the engaged position to urge the shaft against the first gear mechanism and the second gear mechanism.

6. A bone clamp for securing a surgical instrument to a bone, comprising:
   a body on which the instrument can be mounted;
   first and second contacting arms, each of which has a first end pivotally connected to the body, and a second end for gripping the bone, wherein the first and second contacting arms are connected to the body at or towards opposite ends thereof and are configured such that, when the body is positioned adjacent to the bone, the arms can grip the bone on opposite surfaces thereof;
   a threaded shaft releasably engageable with the first and second contacting arms; and
   an actuator movable between an engaged position and a disengaged position, wherein when the actuator is in the disengaged position, the threaded shaft is not engaged with the first and second contacting arms and the first and second contacting arms pivot independently with respect to each other, and when the actuator is in the engaged position, the threaded shaft is engaged with the first and second contacting arms and the first and second contacting arms are configured such that the pivoting movement of one contact arm is accompanied by approximately equal pivoting movement of the other contact arm in the opposite direction.

7. The bone clamp of claim 6, comprising a first gear mechanism operably connected to the first contacting arm at or towards the first end of the first contacting arm and a second gear mechanism operably connected to the second contacting arm at or towards the first end of the second contacting arm.

8. The bone clamp of claim 7, wherein the actuator acts on the shaft when the actuator is in the engaged position to urge the shaft against the first gear mechanism and the second gear mechanism.

9. The bone clamp of claim 7, wherein the actuator comprises a bar configured to extend along the body, and wherein
   (a) when the actuator is in the engaged position, the bar is configured to clamp the shaft tightly between the bar and the body so that the shaft is urged against the first gear mechanism and the second gear mechanism, and
   (b) when the actuator is in the disengaged position, the shaft is able to move away from the first gear mechanism and the second gear mechanism.

10. The bone clamp of claim 9, wherein the actuator comprises a nut configured to engage the body to move the bar relative to the body.

11. The bone clamp of claim 9, comprising a spring disposed between the actuator and the body and wherein, when the actuator is in the disengaged position, the bar is urged towards the body by the spring.

12. The bone clamp of claim 6, wherein the shaft has a first thread extending from one end of the shaft towards the middle, and a second thread extending from the other end of the shaft towards the middle, and wherein one of the shaft threads is a left hand thread and the other of the shaft threads is a right hand thread.

13. The bone clamp of claim 12, wherein the pitch of the first thread is substantially equal to the pitch of the second thread.

14. The bone clamp of claim 6, wherein the second end of each of the first and second contacting arms is configured to grip the bone tissue with which the second end comes into contact when the clamp is in use.

15. The bone clamp of claim 6, wherein the first contacting arm and the second contacting arm are curved.

16. The bone clamp of claim 6 wherein the first and second contacting arms are curved such that the first and second ends of each of the arms are not coplanar with respect to the plane perpendicular to axis of the bone, when the bone clamp is positioned adjacent the bone.

17. The bone clamp of claim 6, comprising a second pair of first and second contacting arms.

18. The bone clamp of claim 17, wherein the first contacting arms of the first and second pairs of contacting arms pivot about a common axis, and wherein the second contacting arms of the first and second pairs of contacting arm pivot about a common axis.

19. The bone clamp of claim 17, wherein the second pair of first and second contacting arms have a shape that differs from the shape of the first pair of contacting arms.

20. The bone clamp of claim 17, wherein the second ends of the first contacting arms are displaced away from each other in a plane parallel to the axis about which the first arms pivot and wherein the second ends of the second contacting arms are displaced away from each other in a plane parallel to the axis about which the second arms pivot.

* * * * *